United States Patent [19]

Schieferstein et al.

[11] Patent Number: 4,814,101

[45] Date of Patent: Mar. 21, 1989

[54] ZWITTERIONIC POLYMERS AND THEIR USE IN HAIR TREATMENT PREPARATIONS

[75] Inventors: Ludwig Schieferstein, Ratingen; Horst Hoeffkes; Kurt Seidel, both of Duesseldorf; Karl Giede, Hilden; Peter Busch, Erkrath, all of Fed. Rep. of Germany

[73] Assignee: Henkel Kommanditgesellschaft auf Aktien, Duesseldorf, Fed. Rep. of Germany

[21] Appl. No.: 169,255

[22] Filed: Mar. 15, 1988

[30] Foreign Application Priority Data

Mar. 16, 1987 [DE] Fed. Rep. of Germany ....... 3708451

[51] Int. Cl.$^4$ .............................................. C11D 3/37
[52] U.S. Cl. .................................. 252/174.23; 252/174; 252/174.24; 252/DIG. 2; 252/DIG. 13; 424/70; 526/292.1; 526/292.6; 526/292.95; 526/258; 526/260; 526/264; 526/265
[58] Field of Search ...................... 252/174.23, 174.24, 252/DIG. 13, DIG. 2, 174; 424/70; 526/292.1, 292.6, 292.95, 258, 260, 264, 265

[56] References Cited

U.S. PATENT DOCUMENTS

| | | | |
|---|---|---|---|
| 3,547,950 | 12/1970 | Gander | 526/292.6 |
| 3,836,537 | 9/1974 | Boerwinkle et al. | 260/29 |
| 3,910,862 | 10/1975 | Barabas et al. | 526/264 |
| 3,914,403 | 10/1975 | Valan | 526/258 |
| 4,012,353 | 3/1977 | Chasin et al. | 526/277 |
| 4,060,678 | 11/1977 | Steckler | 526/260 |
| 4,237,253 | 12/1980 | Jacquet et al. | 526/75 |
| 4,324,780 | 4/1982 | Jacquet et al. | 424/47 |
| 4,454,060 | 6/1984 | Lai et al. | 252/153 |
| 4,455,240 | 6/1984 | Costello | 252/8 |
| 4,460,477 | 7/1984 | Costello | 210/701 |
| 4,484,631 | 11/1984 | Sherwood et al. | 166/274 |
| 4,510,059 | 4/1985 | Amjad et al. | 210/701 |
| 4,533,708 | 8/1985 | Costello | 526/295 |
| 4,702,858 | 10/1987 | Denzinger et al. | 252/174.24 |

Primary Examiner—Paul Lieberman
Assistant Examiner—Hoa Van Le
Attorney, Agent, or Firm—Ernest G. Szoke; Wayne C. Jaeschke; Mark A. Greenfield

[57] ABSTRACT

New zwitterionic polymers are obtained as the copolymerization product of:

from about 30 to about 70 mole % of monomers containing quaternary ammonium groups and corresponding to the following formula:

$$R^1-CH=CR^2-CO-Z-(C_nH_{2n})-N^{(+)}(CH_3)_3;$$

about 10 to about 30 mole % of monomeric carboxylic acids corresponding to the following formula:

$$R^3-CH=CR^4-COOH;$$

about 10 to about 30 mole % of monomeric esters corresponding to the following formula:

$$R^5-CH=CR^6-COOR^7;$$

and, optionally, 0 to about 40 mole % of monomers containing tertiary amino groups and corresponding to the following formula:

$$R^8-CH=CR^9-CO-Z-(C_nH_{2n})-NR^{10}R^{11}.$$

The zwitterionic polymers are suitable for the production of hair-washing and hair-care preparations which have a long-lasting hair-softening effect.

22 Claims, No Drawings

ZWITTERIONIC POLYMERS AND THEIR USE IN HAIR TREATMENT PREPARATIONS

BACKGROUND OF THE INVENTION

1. Field of the Invention

This invention relates to new water-soluble zwitterionic polymers which show high compatibility with anionic and cationic surfactants and good hair-softening and style-holding properties and to their use in hair treatment preparations, more especially in shampoos.

2. Statement of Related Art

Zwitterionic polymers are distinguished by the fact that they contain anionic groups, mostly carboxyl groups and quaternary ammonium groups in the molecule. Numerous zwitterionic polymers are known. It is also known that zwitterionic polymers can be used in hair treatment preparations. U.S. Pat. No. 3,836,537 describes the use of polymers of zwitterionic monomers in hair-setting preparations. The use of copolymers of dimethylaminoethyl methacrylate, acrylic acid and methyl methacrylate in hair-setting preparations and shampoos is described in U.S. Pat. Nos. 4,237,253 and 4,324,780. Zwitterionic copolymers of monomers containing quaternary ammonium groups and monomers containing carboxyl groups are disclosed in U.S. Pat. Nos. 4,544,240, 4,460,477, 4,484,631, 4,510,059 and 4,533,708, where such polymers are recommended as scale and corrosion inhibitors.

The zwitterionic polymers normally used for hair treatment and hair setting preparations have the disadvantage, particularly in formulations containing anionic surfactants, that the hair-softening and hair-setting properties are gradually lost in the event of prolonged storage. Purely cationic water-soluble polymers have the disadvantage that the hair-setting and style-holding properties are not sufficiently pronounced. Accordingly, there is a need to find hair-setting and hair-softening components for hair-treatment preparations, more especially for hair-care and hair-washing preparations, containing anionic surfactants which retain their effect even in the event of prolonged storage in the formulation.

DESCRIPTION OF THE INVENTION

Other than in the operating examples, or where otherwise indicated, all numbers expressing quantities of ingredients or reaction conditions used herein are to be understood as modified in all instances by the term "about".

It has now been found that the requirements stated above are satisfied to a high degree by zwitterionic polymers consisting essentially of:

(A) from 30 to 70 mole % of monomers containing quanternary ammonium groups and corresponding to the following formula:

(I) $R^1—CH=CR^2—CO—Z—(C_nH_{2n})—N^{(+)}(CH_3)_3 A^{(-)}$ wherein $R^1$ and $R^2$ are hydrogen or methyl groups, Z is an oxygen atom or an —NH—group, n is a number from 2 to 5, and $A^{(-)}$ is a chloride, bromide, methoxysulfate or ethoxysulfate anion;

(B) from 10 to 30 mole % of monomeric carboxylic acids corresponding to the following formula:

(II) $R^3—CH=CR^4—COOH$ in which $R^3$ and $R^4$ are hydrogen or methyl groups;

(C) from 10 to 30 mole % of monomeric esters corresponding to the following formula:

(III) $R^5—CH=CR^6—COOR^7$ in which $R^5$ and $R^6$ are hydrogen or methyl groups and $R^7$ is a methyl or ethyl group; and (D) from 0 to 40 mole % of monomers containing tertiary amino groups and corresponding to the following formula:

(IV) $R^8—CH=CR^9—CO—Z—(C_nH_{2n})—NR^{10}R^{11}$ in which $R^8$ and $R^9$ are hydrogen or methyl groups and $R^{10}$ and $R^{11}$ are hydrogen or $C_1$-$C_4$ alkyl groups or, together with the nitrogen atom, form a piperidine, piperazine, pyrrolidine or morpholine ring, Z is an oxygen atom or an —NH—group, and n is a number from 2 to 5.

The zwitterionic polymers according to the invention are readily soluble in water and in aqueous solutions of anionic, cationic, ampholytic, zwitterionic and nonionic surfactants and retain their favorable hair-softening and hair-setting properties in aqueous solutions of anionic surfactants, even in the event of prolonged storage. By virtue of the properties mentioned, the zwitterionic polymers according to the invention are suitable as a setting and hair-softening component in aqueous hair-washing and hair-care preparations. Such preparations include shampoos, rinses, setting lotions, setting gels and also aqueous colorants, permanent-wave preparations or permanent-wave setting preparations.

The zwitterionic polymers according to the invention are prepared from monomers corresponding to formulae (I), (II), (III), and, optionally, (IV) by known polymerization processes in aqueous-alcoholic solution. A radical-forming compound, such as for example potassium or ammonium peroxysulfate, tert.-butyl hydroperoxide, azobis(cyanopentanoic acid) or, preferably, azoisobutyonitrile, is added in small quantities as initiator. The preparation of two copolymers according to the invention is described in the Examples.

Suitable monomers corresponding to formula (I) include derivatives of acrylic acid, methacrylic acid, crotonic acid or 2-methyl crotonic acid. Particularly suitable monomers containing quaternary ammonium groups include methacryloxyethyl trimethyl ammonium methosulfate or methacrylamidopropyl trimethyl ammonium chloride.

Suitable monomeric carboxylic acids corresponding to formula (II) include acrylic acid, methacrylic acid, crotonic acid and 2-methyl crotonic acid. Acrylic acid or methacrylic acid is preferred.

Suitable monomeric esters corresponding to formula (III) include the methyl and ethyl esters of acrylic acid, methacrylic acid, crotonic acid and 2-methyl crotonic acid. The methyl esters of acrylic or methacrylic acid are preferred.

Suitable monomers containing tertiary amino groups corresponding to formula (IV) are preferably acrylic and methacrylic acid derivatives including dimethylaminoethyl methacrylate, dimethylaminopropyl methacrylamide, 2-tert.-butylaminoethyl methacrylate or dimethylaminoneopentyl acrylate.

The most preferred zwitterionic polymers corresponding to the aforementioned formulas consist essentially of:

(A) methacrylamidopropyl trimethyl ammonium chloride (MAPTAC);

(B) acrylic acid (AA) or methacrylic acid (MAA);

(C) methyl acrylate (MA) or methyl methacrylate (MMA); and (D) dimethylaminoethyl methacrylate (DMAEMA).

As indicated above, component A (MAPTAC) may be present at a level of from 30 to 70 mole %, most preferably 30 to 65 mole %. Component B (AA or MAA) is present at a level of from 10 to 30 mole %, most preferably 15 to 25 mole %. Component C (MA or MMA) is present at a level of from 10 to 30 mole %, most preferably 15 to 25% mole %. Component D (DMAEMA) may be present at a level of 0 to 40 mole percent, and, when included, is present at a level of at least 1 mole %, most preferably 30 to 35 mole %.

The properties of the zwitterionic polymers may be modified to obtain an improved hair softening effect through the proportion of component (D), i.e., monomers corresponding to formula (IV). By contrast, zwitterionic polymers containing a particularly high proportion of component (A), i.e. monomers corresponding to formula (I), have a particularly pronounced setting, style-holding effect. Where component (D) is used, it is employed at a level effective to impart minimally hair softening properties to the composition.

It is particularly preferred to use at least one zwitterionic polymer according to the invention in aqueous preparations containing at least one anionic surfactant. Accordingly, one preferred embodiment of the invention is a water-based hair shampoo which is characterized in that it contains from 0.1 to 10% by weight of a zwitterionic polymer according to the invention and from 5 to 25% by weight of an anionic surfactant.

Suitable anionic surfactants in hair treatment preparations according to the invention are any anionic surface-active compounds suitable for use on the human body. These compounds are characterized by a water-solubilizing, anionic group such as, for example, a carboxylate, sulfate, sulfonate or phosphate group, and a lipophilic alkyl group containing from 10 to 22 carbon atoms. In addition, glycol or polyglycol ether groups, ester, ether and amide groups and also hydroxyl groups may be present in the molecule. Examples of suitable anionic surfactants are the sodium, potassium, ammonium, mono-, di- and tri-alkanolammonium salts containing 2 or 3 carbon atoms in the alkanol group of:

linear $C_{10}$–$C_{22}$ fatty acids (soaps), ether carboxylic acids corresponding to the formula $R^1$—O—$(CH_2$—$CH_2O)_x$—$CH_2$—COOH, in which $R^1$ is a linear $C_{10}$–$C_{22}$ alkyl group and x is 0 or 1 to 10;

acyl sarcosines containing from 10 to 18 carbon atoms in the acyl group;

acyl taurides containing from 10 to 18 carbon atoms in the acyl group;

acylisethionates containing from 10 to 18 carbon atoms in the acyl group;

sulfosuccinic acid mono- and dialkyl esters containing from 8 to 18 carbon atoms in the alkyl group and sulfosuccinic acid monalkyl polyoxyethyl esters containing from 8 to 18 carbon atoms in the alkyl group and from 1 to 6 oxyethyl groups;

linear $C_{12}$–$C_{18}$ alkane sulfonates;

linear $C_{12}$–$C_{18}$ alpha-olefin sulfonates;

alpha-sulfofatty acid methyl esters of $C_{12}$–$C_{18}$ fatty acids;

alkyl sulfates and alkyl polyglycol ether sulfates corresponding to the formula $R^1$—O$(CH_2$—$CH_2O)_x$—$OSO_3H$, in which $R^1$ is a preferably linear $C_{10}$–$C_{18}$ alkyl group and x is 0 or 1 to 12.

Alkyl sulfates and alkyl polyglycol ether sulfates containing from 10 to 18 carbon atoms in the alkyl group and up to 12 glycol ether groups in the molecule are particularly preferred.

In addition to the anionic surfactants mentioned, the hair shampoo formulations according to the invention may contain any of the auxiliaries and additives normally used for this purpose in the usual quantities. Such auxiliaries and additives are, in particular, nonionic, amphoteric and zwitterionic surfactants.

Nonionic surfactants are, above all, the adducts of from 2 to 20 moles ethylene oxide with preferably linear $C_{12}$–$C_{18}$ alcohols, with alkylphenols containing from 8 to 15 carbon atoms in the alkyl group, with $C_{12}$–$C_{18}$ fatty acids, with fatty acid partial glycerides, with fatty acid sorbitan partial esters, with fatty acid alkanolamides and with methyl glucoside fatty acid esters. Other suitable nonionic surfactants are alkyl (oligo)glucosides, alkylamine oxide surfactants and fatty acid alkanolamines. Examples of amphoteric surfactants are alkyl ($C_8$–$C_{18}$)-trimethyl-ammonioglycinate or acyl ($C_8$–$C_{18}$)-aminopropyl trimethyl-ammonioglycinate.

Certain cationic surfactants compatible with anionic surfactants may also be present in the hair shampoos according to the invention. Examples of such cationic surfactants are disclosed in German patent document No. 3442175.

In addition to the zwitterionic surfactants, the aqueous hair-washing and hair-care preparations according to the invention may also contain any of the auxiliaries and additives normally used for the particular application envisaged.

In the case of hair rinses, such auxiliaries and additives include cationic surfactants, more especially surface-active quaternary ammonium salts, $C_{12}$–$C_{22}$ fatty alcohols, fatty acid partial glycerides, cosmetic oil and fatty components and water-soluble polymers having a thickening effect; for setting lotions and setting gels, they include cationic surfactants, cationic, nonionic or anionic polymers and lower alcohols. Hair dyes generally contain substantive dyes or oxidation dye precursors, anionic or nonionic surfactants, ammonia or alkanolamines and, optionally, antioxidants. Permanent-wave setting preparations generally contain an oxidizing agent such as $H_2O_2$, $H_2O_2$ adducts, or potassium bromate, and also include anionic or nonionic surfactants.

The zwitterionic polymers according to the invention are present in the aqueous hair-washing and hair-care preparations mentioned above in a quantity of from 0.1 to 10% by weight, and more preferably from 0.1 to 2% by weight.

The following Examples are intended to illustrate the invention without limiting it in any way.

EXAMPLE 1

Preparation of a copolymer of 3 moles MAPTAC, 1 mole acrylic acid and 1 mole methyl methacrylate:

2.4 kg methyl methacrylate (MMA) and 16.0 kg isopropanol were introduced into a reactor equipped with an impeller stirrer, a heating system, a cooling system, a reflux and head condenser and a thermometer and 0.1 kg azoisobutyronitrile was dissolved therein with stirring. 31 kg of a 50% by weight aqueous solution of methacrylamidopropyl trimethyl ammonium chloride (MAPTAC), 1.7 kg acrylic acid (AA) and 47.2 kg water were then added. The mixture was adjusted to pH 7.0 with approximately 1.6 kg ammonia solution (25% by weight in water).

The contents of the reactor were then stirred for 30 minutes at a jacket temperature of 65° C., resulting in slight heating. The mixture was then heated to 80° C. and stirred for another 2 hours. On completion of the reaction, 20 kg water were added and the same quantity distilled off again under normal pressure (1 bar) in the form of an azeotrope. After cooling to 30° C., the polymer solution had the following characteristic data:

| | |
|---|---|
| pH value | 6.8 |
| Dried acetone precipitate | 125% of the theoretical |
| Specific viscosity (1% in 1N NaNO$_3$ solution) | 0.65 |

EXAMPLE 2

Preparation of a copolymer of 2 moles MAPTAC, 1 mole acrylic acid, 1 mole methyl methacrylate and 2 moles DMAEMA:

2.1 kg methyl methacrylate and 16.0 kg isopropanol were introduced into a reactor equipped with an impeller stirrer, a heating system, a cooling system, a reflux and head condenser and a thermometer and 0.1 kg azoisbutyronitrile was dissolved therein with stirring. 18.3 kg of a 50% by weight aqueous solution of methacrylamidopropyl trimethyl ammonium chloride (MAPTAC), 6.5 kg dimethylaminoethyl methacrylate (DMAEMA) and 52.9 kg water were then added. After the careful addition of 1.5 kg acrylic acid, the mixture was adjusted to pH 7.0 with approximately 2.6 kg dilute sulfuric acid (30% by weight in water) and heated to 65° C. After stirring for 30 minutes at that temperature, resulting in slight heating, the mixture was heated to 80° C. and stirred for another 2 hours. 20 kg water were then added and the same quantity distilled off again under normal pressure (1 bar) in the form of an azeotrope. After cooling to 30° C., the polymer solution showed the following characteristic data:

| | |
|---|---|
| pH value | 6.9 |
| Dried acetone precipitate | 145% of the theoretical |
| Specific viscosity (1% in 1N NaNO$_3$ solution) | 0.65 |

EXAMPLES 3–9

The following examples illustrate the composition of various hair-care products prepared by forming aqueous dispersions of the listed compositions by techniques well known in the art. All of these products are considered effective for their indicated purposes.

| 3. Hair Shampoo | % by weight |
|---|---|
| Fatty alcohol(C$_{12-14}$) poly(3 EO) glycolether sulfate, Na salt, 28% aqueous solution | 30 |
| Coconut acyl(C$_{12-18}$)-aminopropyl dimethyl glycine, 30% aqueous solution | 20 |

-continued

| 3. Hair Shampoo | % by weight |
|---|---|
| Copolymer solution Example 1 (approx. 20%) | 5 |
| Water adjust to | 100% |

| 4. Hair rinse | % by weight |
|---|---|
| Fatty alcohol(C$_{12-14}$) poly(3 EO) glycol ether sulfate, Na salt, 28% aqueous solution | 5 |
| Copolymer solution Example 2 (approx. 20%) | 2 |
| Water adjust to | 100% |

| 5. Hair rinse | % by weight |
|---|---|
| N—(2-hydroxyhexadecyl-1-)-N,N—dimethyl-(2-hydroxyethyl)-ammonium chloride, 28% aqueous solution | 4 |
| Copolymer solution Example 2 (approx. 20%) | 5 |
| Water adjust to | 100% |

| 6. Hair setting gel | % by weight |
|---|---|
| N—(2-hydroxyhexadecyl-1-)-N,N—dimethyl-N—(2-hydroxyethyl)-ammonium chloride, 28% aqueous solution | 0.2 |
| Isopropanol | 15.0 |
| copolymer solution Example 2 (approx. 20%) | 6.0 |
| Water adjust to | 100% |

| 7. Hair setting lotion | % by weight |
|---|---|
| Polyvinylpyrrolidone-polyvinyl acetate copolymer (60:40) | 1.4 |
| Copolymer solution Example 1 (approx. 20%) | 4.0 |
| Ethanol | 20.0 |
| Water adjust to | 100% |

| 8. Hair dye | % by weight |
|---|---|
| Tallow fatty alcohol (C$_{16-18}$) | 8.0 |
| Fatty alcohol(C$_{12-14}$)poly(3 EO) glycol ether sulfate, Na salt, 28% aqueous solution | 20.0 |
| Copolymer solution Example 1 (approx. 20%) | 2.5 |
| Oxidation dye precursors | 2.0 |
| Water adjust to | 100% |

| 9. Permanent-wave setting preparation | % by weight |
|---|---|
| Potassium bromate | 5.0 |
| Fatty alcohol(C$_{12-14}$)poly(3 EO)glycol ether sulfate, Na salt, 28% aqueous solution | 5.0 |
| Citric acid sufficient to adjust to a pH of | 4 |
| Copolymer solution Example 2 (approx. 20%) | 1.5 |
| Water adjust to | 100% |

It is to be understood that the above described embodiments of the invention are illustrative only and that modifications throughout may occur to those skilled in the art.

We claim:

1. A zwitterionic polymer prepared by copolymerizing a monomer mix consisting essentially of:
   (A) from about 30 to about 70 mole % of monomers containing quaternary ammonium groups and corresponding to the following formula:

$$R^1-CH=CR^2-CO-Z-(C_nH_{2n})-N^{(+)}(CH_3)_3A^{(-)}$$

wherein $R^1$ and $R^2$ are hydrogen or methyl groups, Z is an oxygen atom or an —NH—group, n is a number from 2 to 5 and $A^{(-)}$ is a chloride, bromide, methoxysulfate or ethoxysulfate anion;
   (B) from about 10 to about 30 mole % of monomeric carboxylic acids corresponding to the following formula:

$$R^3-CH=CR^4-COOH$$

wherein $R^3$ and $R^4$ are hydrogen or methyl groups;
   (C) from about 10 to about 30 mole % of monomeric esters corresponding to the following formula:

$$R^5-CH=CR^6-COOR^7$$

wherein $R^5$ and $R^6$ are hydrogen or methyl groups and $R^7$ is a methyl or ethyl group; and
   (D) from 0 to about 40 mole % of monomers containing tertiary amino groups and corresponding to the following formula:

$$R^8-CH=CR^9-CO-Z-(C_nH_{2n})-NR^{10}R^{11}$$

wherein $R^8$ and $R^9$ are hydrogen or methyl groups and $R^{10}$ and $R^{11}$ are hydrogen or $C_1-C_4$ alkyl groups or, together with the nitrogen atom, form a piperidine, piperazine, pyrrolidine or morpholine ring, Z is an oxygen atom or an —NH—group and n is a number from 2 to 5.

2. The polymer of claim 1 wherein component A is methylacrylamidopropyl trimethyl ammonium chloride.

3. The polymer of claim 2 wherein said component A is present at a level of from about 30 to about 65 mole %.

4. The polymer of claim 1 wherein component B is acrylic acid or methacrylic acid.

5. The polymer of claim 4 wherein component B is present at a level of from about 15 to about 25 mole %.

6. The polymer of claim 4 where component B is acrylic acid.

7. The polymer of claim 1 wherein component C is methyl acrylate or methyl methacrylate.

8. The polymer of claim 7 wherein component C is present at a level of from about 15 to about 25 mole %.

9. The polymer of claim 7 wherein component C is methyl methacrylate.

10. The polymer of claim 1 wherein component D is dimethylaminoethyl methacrylate present at a level of at least about 1 mole %.

11. The polymer of claim 10 wherein component D is present at a level of from about 30 to about 35 mole %.

12. The polymer of claim 1 wherein the monomer mix consists essentially of:
    (A) from about 30 to about 70 mole % of methylacrylamidopropyl trimethyl ammonium chloride;
    (B) from about 10 to about 30 mole % of acrylic or methacrylic acid;
    (C) from about 10 to about 30 mole % of methyl acrylate or methyl methacrylate; and
    (D) from 0 to about 40 mole % of dimethylaminoethyl methacrylate.

13. The polymer of claim 12 wherein component D is present at a level of from about 30 to about 35 mole %.

14. An aqueous hair-care composition containing at least one polymer of claim 1 in an amount effective to impart hair-setting or hair-softening properties into said composition.

15. An aqueous hair-care composition containing at least one polymer of claim 12 in an amount effective to impart hair-setting or hair-softening properties into said composition.

16. A water-based hair shampoo comprising from about 0.1 to about 10% by weight of at least one zwitterionic polymer of claim 1 and from about 5 to about 25% by weight of an anionic surfactant.

17. The shampoo of claim 16 wherein the anionic surfactant is at least one alkyl sulfate or alkyl polyglycol ether sulfate corresponding to the following formula:

$$R^1-(OCH_2CH_2)_z-OSO_3^{(-)}M^{(+)}$$

wherein $R^1$ is a linear $C_{10}-C_{18}$ alkyl group, z is 0 or a number from 1 to 10, and $M^{(+)}$ is a lithium, sodium, potassium, magnesium, ammonium, mono-, di- or trialkanol-ammonium ion containing 2 or 3 carbon atoms in the alkanol group.

18. A water-based hair rinse comprising from about 0.1 to about 10% by weight of at least one zwitterionic polymer of claim 1.

19. A water-based hair setting gel comprising from about 0.1 to about 10% by weight of at least one zwitterionic polymer of claim 1.

20. A water-based hair setting lotion comprising from about 0.1 to about 10% by weight of at least one zwitterionic polymer of claim 1.

21. A water-based dye comprising from about 0.1 to about 10% by weight of at least one zwitterionic polymer of claim 1.

22. A water-based permanent wave setting preparation comprising from about 0.1 to about 10% by weight of at least one zwitterionic polymer of claim 1.

* * * * *